(12) United States Patent
Pereira et al.

(10) Patent No.: US 7,976,830 B2
(45) Date of Patent: *Jul. 12, 2011

(54) FATTY QUAT BASED ON ANTE-ISO COMPOUNDS

(75) Inventors: Abel G. Pereira, Bridgewater, NJ (US); Helena S. Barinova, Iselin, NJ (US)

(73) Assignee: Croda, Inc., Edison, NJ (US)

( * ) Notice: Subject to any disclaimer, the term of this patent is extended or adjusted under 35 U.S.C. 154(b) by 1791 days.

This patent is subject to a terminal disclaimer.

(21) Appl. No.: 11/036,661

(22) Filed: Jan. 14, 2005

(65) Prior Publication Data
US 2005/0123498 A1  Jun. 9, 2005

Related U.S. Application Data

(63) Continuation of application No. 10/430,143, filed on May 6, 2003, now abandoned, which is a continuation-in-part of application No. 09/821,512, filed on Mar. 29, 2001, now Pat. No. 6,562,328.

(60) Provisional application No. 60/192,839, filed on Mar. 29, 2000.

(51) Int. Cl.
  *A61Q 5/00*  (2006.01)
  *A61Q 5/12*  (2006.01)
  *A61K 8/02*  (2006.01)

(52) U.S. Cl. ............... 424/70.1; 424/70.27; 424/401

(58) Field of Classification Search ........... 424/70.1, 424/70.27, 401
See application file for complete search history.

(56) References Cited

U.S. PATENT DOCUMENTS

| | | | | |
|---|---|---|---|---|
| 4,069,347 A | * | 1/1978 | McCarthy et al. | 514/788 |
| 4,631,187 A | | 12/1986 | Padden et al. | |
| 4,954,335 A | | 9/1990 | Janchipraponvej | |
| 4,976,956 A | | 12/1990 | Noe | |
| 5,476,649 A | * | 12/1995 | Naito et al. | 424/70.1 |
| 5,635,469 A | | 6/1997 | Fowler et al. | |
| 5,683,685 A | | 11/1997 | Hirano et al. | |
| 5,747,015 A | | 5/1998 | Oshika et al. | |
| 6,388,111 B1 | | 5/2002 | Pereira et al. | |
| 6,399,799 B1 | | 6/2002 | Pereira | |
| 6,500,791 B2 | | 12/2002 | Pereira | |
| 6,562,328 B2 | * | 5/2003 | Pereira et al. | 424/70.28 |

FOREIGN PATENT DOCUMENTS

| | | | |
|---|---|---|---|
| DE | 43 34 365 A | | 4/1995 |
| EP | 0 129 014 A | | 12/1984 |
| EP | 0 596 135 A1 | * | 11/1993 |
| EP | 0 596 135 | * | 5/1994 |
| EP | 0 596 135 A | | 5/1994 |
| EP | 0 682 935 A | | 11/1995 |
| EP | 0 705 604 A | | 4/1996 |
| JP | 63 066125 A | | 3/1988 |
| JP | 04 164014 A | | 6/1992 |
| JP | 04 295 423 A | | 10/1992 |
| JP | 6-234994 A | | 8/1994 |
| JP | 9-143135 A | | 6/1997 |
| WO | WO-98/30532 A | | 7/1998 |

OTHER PUBLICATIONS

Office Action from Japanese Applicatoin No. 2001-570231 issued Apr. 23, 2011.

* cited by examiner

*Primary Examiner* — Blessing M Fubara
(74) *Attorney, Agent, or Firm* — Lerner, David, Littenberg, Krumholz & Mentlik, LLP

(57) ABSTRACT

The invention discloses quaternary ante-iso acids useful as additives in personal care products. Various quaternary derivatives of ante-sio acids are described, and examples of their use in personal care composition are presented.

18 Claims, No Drawings

FATTY QUAT BASED ON ANTE-ISO COMPOUNDS

CROSS REFERENCE TO RELATED APPLICATIONS

The present application is a continuation of U.S. patent application Ser. No. 10/430,143, filed May 6, 2003, which is a divisional application of U.S. Pat. application Ser. No. 09/821,512 filed Mar. 29, 2001, which itself claims the benefit of U.S. Provisional Patent Application No. 60/192,839, filed Mar. 29, 2000, all of which are incorporated herein by reference in their entirety.

FIELD OF THE INVENTION

The present invention relates to the field of quaternary ammonium compounds ("quats") and, in particular, their use in additives for personal care products such as shampoos, conditioners, skin care products and the like.

BACKGROUND OF THE INVENTION

Human hair contains a thin protective fatty layer of an ante-iso fatty acid, 18-methyl eicosanoic acid (18-MEA), covalently bound to the cuticle. Chemical or mechanical damage to the hair removes portions of this fatty layer making the hair less manageable, less healthy looking and more susceptible to environmental stresses. In the treatment of hair, it is desirable to replenish these ante-iso fatty acids, particularly 18-MEA.

18-MEA is relatively rare in nature and is found in small amounts in materials such as lanolin. Lanolin contains a mixture of fatty acids, including amongst other things, ante-iso fatty acids, as well as hydroxy fatty acids, iso-hydroxy fatty acids, iso fatty acids and unsubstituted fatty acids. U.S. Pat. No. 4,069,347, issuing to McCarthy et al., discloses compositions of quat derivatives of fatty acids derived from lanolin. These lanolin-derived quats are described as being useful, when combined with specific branched-diols, in the preparation of clear cosmetic formulations. These include shampoos and clear hair rinse formulations.

SUMMARY OF THE INVENTION

In one aspect, the present invention relates to quats derived from either fatty acid compounds consisting essentially of ante-iso fatty acids or fatty acid mixtures enriched in ante-iso fatty acids.

These quats impart desirable properties when used as additives to personal care products including hair grooming preparations and skin care products. Personal care products which include an additive of quats consisting essentially of ante-iso fatty acids or comprising fatty acid mixtures enriched in ante-iso fatty acid content are also contemplated.

A number of new discoveries have been made with important consequences for personal care products. First, it has been discovered that of all the various components contained in lanolin, it is the ante-iso fatty acids which, when quaternized, have the most profound effect upon the health and manageability of hair and/or skin. It has also been discovered that additives which consist essentially of quats of one or more ante-iso fatty acids, without significant quantities (greater than 5%) of the quats of other fatty acid species traditionally found in lanolin, yield superior personal care products. Of course, the personal care products containing these quat based additives can, and often will, include other fatty acids and fatty acid quats in varying amounts for other reasons.

It has further been discovered that of these ante-iso fatty acids, 18-MEA (having a C-21 chain), is particularly useful and provides dramatically improved results over, for example, quaternized lanolin acids derived directly from lanolin. Thus, additives containing a relatively large proportion of 18-MEA when compared to, for example, lanolin are extremely effective additions to personal care products.

However, these ante-iso fatty acids and, in particular, 18-MEA, are not typically found in nature in large quantities. These materials are also generally not found in sources from which they can be easily extracted in large quantities. U.S. Pat. No. 5,476,649, issuing to Naito et al., the text of which is hereby incorporated by reference, discloses various synthetic methods for preparation of ante-iso acids. The various synthetic preparations disclosed all call for the use of reagents and solvents such as benzene, xylene, triphenylphosphine, phosphorous tribromide, etc., that create handling and disposal difficulties due to their toxicity. These manufacturing procedures are difficult, time consuming, costly and solvent intensive. Still, where available, additives produced almost exclusively from ante-iso fatty acid quats, particularly those with fatty acid chains longer than 15 carbon atoms, and more preferably those made with 18-MEA, are desirable.

While it is desirable to make and use additives of quats made almost exclusively from ante-iso fatty acids, it has also been unexpectedly found that significant improvements in hair and skin care products, make-up, cosmetics and the like, can be obtained without the need for formulations limited to substantially only these quats. Desirable and unexpected results are also obtained by using quats resulting from mixtures of ante-iso acids with other fatty acid species, such as the mixtures that are found in lanolin, so long as the content of the ante-iso acids, and accordingly, the content of their corresponding quats, is enriched relative to lanolin. This can be done by, for example, processing lanolin acids, such as those disclosed in McCarthy et al., U.S. Pat. No. 4,069,347, the text of which is incorporated herein by reference, and enriching them by the addition of more ante-iso acid quats such as those produced in Naito et al. A relative increase in the content of ante-iso fatty acids can also be accomplished by removing some quantity of less desirable fatty acid species, such as by concentration techniques like molecular distillation. This approach can be accomplished without the use of solvents. When concentrating, for example, lanolin acids, it is most preferred to use techniques which result in a decrease in the relative proportion of iso-hydroxy fatty acids and hydroxy fatty acids thereby enriching the relative proportion of the ante-iso fatty acids.

It has also been found that many quats produced from ante-iso enriched mixtures are compatible with anionic surfactants. For the purposes of this application, "compatible with anionic surfactants" means that a clear solution, one without significant precipitation or turbidity, results once the quat is mixed with the surfactant. This is surprising since it was previously thought that with standard lanolin acid quats, such as those described in McCarthy et al., it was the presence of significant amounts of hydroxy fatty acid quats that made them anionic surfactant compatible. Since in accordance with the present invention, the iso-hydroxy fatty acids and the hydroxy fatty acids are generally removed, or their relative proportions reduced, it is completely unexpected to see continued anionic surfactant compatibility.

DETAILED DESCRIPTION OF THE PREFERRED EMBODIMENTS

Ante-iso acids conform to the following formula:

where "z" can be any positive whole number, and R is an alkyl group, substituted or un-substituted, straight chain or branched, saturated or unsaturated. This alkyl group may be substituted or unsubstituted.

Hydroxy fatty acids include at least one —OH group attached to the fatty acid chain. Iso fatty acids are similar to ante-iso fatty acids except that the attached alkyl group is located closer to the carbon furthest from the carbonyl group, usually on the next adjacent carbon.

The ante-iso acids used to produce the quat compounds in accordance with the present invention can be individually essentially pure (either all ante-iso fatty acids or a mixture of substantially only ante-iso fatty acids) or part of a fatty acid mixture that is generally comprised of acids illustrated, by example in Table I.

TABLE I

| Carbon Chain | Ante-iso Acids(%) | Normal Acids (%) | Iso-Acids |
|---|---|---|---|
| $C_{8-15}$ | <5 | <5 | <5 |
| $C_{16}$ | 0-10 | 0.1-20 | 0.1-20 |
| $C_{17}$ | 0-5 | 0-5 | 0.1-10 |
| $C_{18}$ | 0-10 | 0.1-20 | 0.1-20 |
| $C_{19}$ | 0-50 | 0-10 | 0-10 |
| $C_{20}$ | 0-5 | 0-10 | 1-40 |
| $C_{21}$ | 0-95 | 0-5 | 0-5 |
| $C_{22}$ | 0-5 | 0-10 | 1-20 |
| $C_{23}$ | 0-25 | 0-5 | 0-10 |
| $C_{24}$ | 0-5 | 1-15 | 1-20 |
| $C_{25}$ | 0-30 | 0.1-10 | 0.1-10 |
| $C_{26}$ | 0-5 | 0.1-10 | 0.1-20 |
| $C_{27}$ | 0-10 | 0-5 | 0-5 |
| TOTAL | 8-95 | 1.5-50 | 3.5-60 |

In the present application, hydroxy fatty acids or iso-hydroxy fatty acids are preferably minimized to levels at least about 10% lower than that typically found in lanolin and more preferably substantially eliminated. Additionally, the ante-iso fatty acids are preferably kept at levels greater than those typically found in lanolin, more preferably at levels at least about 10% greater than those typically found in lanolin.

A more preferred fatty acid mixture useful to produce quats in accordance with the present invention has a fatty acid content distribution as shown in Table II below.

TABLE II

| Carbon Chain | Ante-iso Acids(%) | Normal Acids(%) | Iso-Acids(%) |
|---|---|---|---|
| $C_{8-15}$ | <3 | <3 | <3 |
| $C_{16}$ | 1-5 | 0.2-10 | 0.2-10 |
| $C_{17}$ | 0-3 | 0-3 | 0.2-5 |
| $C_{18}$ | 1-5 | 0.2-10 | 0.2-10 |
| $C_{19}$ | 4-25 | 1-5 | 1-5 |
| $C_{20}$ | 0-3 | 1-5 | 2-20 |
| $C_{21}$ | 7-50 | 0-3 | 0-3 |
| $C_{22}$ | 0-3 | 1-5 | 2-10 |
| $C_{23}$ | 2-15 | 0-3 | 1-5 |
| $C_{24}$ | 0-3 | 2-10 | 2-10 |

TABLE II-continued

| Carbon Chain | Ante-iso Acids(%) | Normal Acids(%) | Iso-Acids(%) |
|---|---|---|---|
| $C_{25}$ | 2-20 | 0.2-5 | 0.2-5 |
| $C_{26}$ | 0-3 | 0.2-5 | 1-10 |
| $C_{27}$ | 0-10 | 0-5 | 0-5 |
| TOTAL | 15-75 | 10-50 | 10-50 |

For purposes of comparison, a typical distribution of the fatty acids contained in lanolin acids is shown in Table III below.

TABLE III

| Carbon Chain | Ante-iso Acids(%) | Normal Acids (%) | Iso-acids | Hydroxy-Acids (%) | Iso-Hydroxy Acids (%) |
|---|---|---|---|---|---|
| $C_{10}$ | 0 | 0.27 | 0.31 | 0 | 0 |
| $C_{11}$ | 0.80 | 0 | 0 | 0 | 0 |
| $C_{12}$ | 0 | 0.29 | 0.92 | 0 | 0 |
| $C_{13}$ | 0 | 0 | 1.20 | 0 | 0 |
| $C_{14}$ | 0 | 1.51 | 1.93 | 2.0 | 0.23 |
| $C_{15}$ | 3.07 | 0.47 | 0.31 | 0.91 | 0.54 |
| $C_{16}$ | 0.30 | 2.73 | 2.19 | 20.77 | 0.82 |
| $C_{17}$ | 1.69 | 0 | 0.23 | 0.21 | 0 |
| $C_{18}$ | 0 | 1.58 | 2.37 | 1.41 | 6.97 |
| $C_{19}$ | 4.30 | 0 | 0 | 0.76 | 0 |
| $C_{20}$ | 0 | 0.80 | 4.0 | 0.42 | 0 |
| $C_{21}$ | 3.81 | 0 | 0 | 0 | 0 |
| $C_{22}$ | 0 | 0.77 | 1.99 | 0.25 | 0 |
| $C_{23}$ | 1.28 | 0 | 0 | 0 | 0 |
| $C_{24}$ | 0 | 2.42 | 1.95 | 0 | 0 |
| $C_{25}$ | 0 | 0 | 3.23 | 0 | 0 |
| $C_{26}$ | 0 | 1.08 | 2.0 | 0 | 0 |
| $C_{27}$ | 1.22 | 0 | 0 | 0 | 0 |
| TOTAL | 17.67 | 12.87 | 21.43 | 26.73 | 8.56 |

As is evident from Table III, the fatty acid distribution of typical lanolin acids contains greater than 35% hydroxy fatty acids and iso-hydroxy fatty acids. It is desirable to reduce or eliminate these hydroxy fatty acid and iso-hydroxy fatty acid species, thereby increasing the concentration of the ante-iso fatty acids. Alternatively, either other fatty acid species can be eliminated or additional ante-iso fatty acids can be added to enrich the relative proportion of ante-iso fatty acids.

The quaternary compounds in accordance with the present invention may, for example, have the formula (I):

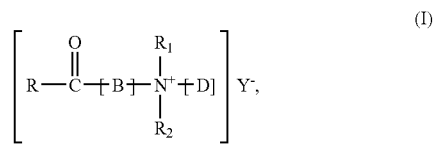

where R is

$R_3$ is an alkyl group, straight chain or branched, saturated or unsaturated, z may vary from 0 to 30; B is any organic group connecting group R to the quaternized nitrogen; D is any organic group attached to the quaternized nitrogen in any manner; $R_1$ and $R_2$, are each independently alkyl or alkoxy quaternizing group, same or different; $Y^-$ is a counter ion. Preferably, R is an alkyl group having from 8 to 30 carbon atoms; z ranges from 3 to 25, more preferably z ranges from 5 to 22, most preferably z is 16; $R_3$ has up to 12 carbon atoms, more preferably, from 1 to 6 carbon atoms, most preferably $R_3$ is methyl. Preferably, B and D contains C, H, N, and O atoms; $Y^-$ is halogen-, sulfur- or nitrogen-containing anion; most preferably halogen, sulfate, sulfite, sulfide or nitro anion.

The specific quaternary compounds in accordance with the invention may, for example, have the formula (II):

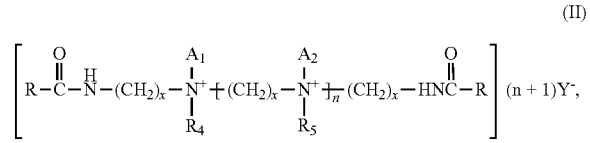

where at least one of R is

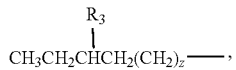

$R_3$ is an alkyl group, straight chain or branched, saturated or unsaturated, z may vary from 0 to 30; each $A_1$ and $A_2$, same or different, are independently alkoxy or lower alkyl; z may vary from 0 to 30; $R_4$ and $R_5$ are alkyl groups, same or different; n may range from 0 to 10, x may range from 1 to 6; $Y^-$ are counter ions; if only one R is

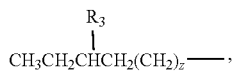

then another R is an alkyl group, straight chain or branched, aromatic or aliphatic, saturated or unsaturated, substituted or un-substituted, having up to 30 carbon atoms. Preferably, when R is

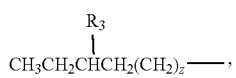

R has from 8 to 30 carbon atoms, preferably z ranges from 3 to 25, more preferably z ranges from 5 to 22, most preferably z is 16; if only one R is

then another R is preferably an aliphatic alkyl group having 12 to 24 carbon atoms, more preferably 14 to 22 carbon atoms; $R_4$ and $R_5$ are independently lower alkyl groups, more preferably methyl or ethyl, most preferably $R_4$ and $R_5$ are both methyl; $A_1$ and $A_2$ are each independently ethoxy, polyethoxy, propoxy, methyl or lower alkyl having from 1 to 6 carbon atoms; $R_3$ is a alkyl group having up to 12 carbon atoms, more preferably from 1 to 6 carbon atoms, most preferably methyl; $Y^-$ are halogen-, sulfur- or nitrogen-containing anions; most preferably halogens, sulfates, sulfites, sulfides, or nitro anions. Most preferably R is derived from 18-methyl eicosanoic acid, i.e., $R_3$ is methyl, and z is 16.

Other specific quaternary compounds in accordance with the invention may also, for example, have the formula (III):

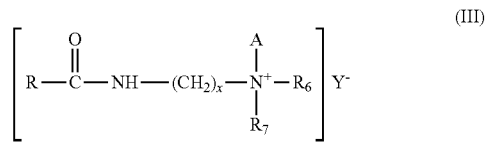

where R groups is

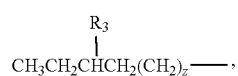

$R_3$ is an alkyl group, straight chain or branched, saturated or unsaturated, z may vary from 0 to 30; $R_6$ and $R_7$, same or different, are each independently aromatic or aliphatic alkyl group, straight chain or branched, saturated or unsaturated, or an alkoxy group; x ranges from 1 to 6; A is alkoxy or lower alkyl; $Y^-$ is a counter ion. Preferably, R is an alkyl group having from 8 to 30 carbon atoms; z ranges from 3 to 25, more preferably z ranges from 5 to 22, most preferably z is 16; $R_3$ is a alkyl group having up to 12 carbon atoms, more preferably from 1 to 6 carbon atoms, most preferably methyl; $R_6$ and $R_7$, same or different, are each independently aromatic or aliphatic alkyl group having from 1 to 8 carbon atoms, or ethoxy, polyethoxy, propoxy or polypropoxy group; A is ethoxy, polyethoxy, propoxy or polypropoxy, or lower alkyl having 1 to 6 carbon atoms; $Y^-$ is halogen-, sulfur- or nitrogen-containing anions; most preferably, halogen, sulfate, sulfite, sulfide, or nitro anion. Most preferably R is derived from 18-methyl eicosanoic acid, i.e., $R_3$ is methyl, and z is 16.

The quats in accordance with the present invention can be made by any technique such as, without limitation, the procedures described in U.S. patent application Ser. No. 09/409,203 ("'203 application"), by inventors Pereira and Barinova, or U.S. patent application. Ser. No. 09/409,204 ("'204 application"), by inventors Pereira and Nikolopolous. These two applications were filed on Sep. 30, 1999 and are assigned to the assignee of the present application. The contents of these applications are hereby incorporated by reference herein.

The '203 application describes an exemplary synthesis in which the quats are prepared by first reacting fatty acid and diethylenetriamine (DETA) or similar amine species. The product should then be cooled and ethylene oxide should be added. After the ethylene oxide has reacted sufficiently, the batch should be further cooled and then quaternized in the presence of propylene glycol, butylene glycol, isopropyl alcohol and the like with dimethyl sulfate, methyl chloride, benzyl chloride and the like or any other quaternizing agent generally known to those skilled in the art.

The '204 application describes an exemplary synthesis in which the quats are prepared by reacting fatty acids, oils, triglycerides, or mixtures thereof, with dialkyl amines such as gamma dimethylamino-propylamine (DMAPA), gamma diethylamino-propylamine (DEAPA) using an alkaline catalyst such as sodium hydroxide to produce an amidoamine. The appropriate amidoamine is then quaternized with either ethylene chlorohydrin or ethylene bromohydrin in a solvent mixture such as water and propylene glycol.

As discussed above, various amine species are useful to produce quats in accordance with the present invention including, without limitation, dialkyl amines such as diethylenetriamine (DETA), gamma dimethylamino-propylamine (DMAPA), gamma diethylamino-propylamine (DEAPA) or triethylene tetraamine (TETA).

These quats traditionally are present with counter ions. Counter ions can include any known to be useful with quaternized amino amines such as, for example, and without limitation, chlorine, bromine, etc.

Quats can also be formulated in a varying range of cationic activities. The cationic activity of a quat is used to measure the content of the quats disbursed or dissolved in the solvent in a percent by weight basis. Thus, a quat that has 50% cationic activity is provided in a 50% weight ratio to the solvent. Generally, it is preferred that a higher percent cationic activity be provided. This can be done by diluting or concentrating solutions of the quats prepared in accordance with the present invention as is known in the art. While water can be used as a carrier or solvent, other useful carriers include glycols or polyglycols, fatty alcohols, alkoxy alcohols, or any mixtures of these solvents. Other useful solvent mixtures can be found in U.S. patent application Ser. No. 09/438,631 by inventors Barinova, Nikolopolous and Pereira. This application was filed on Nov. 12, 1999, is assigned to the assignee of the present application, and is hereby incorporated by reference herein.

It is also preferable that the resulting quats be flakeable or pastillatable. Whether a formulation is flakeable is measured by pouring a relatively thin film (1/16"-1/8") of a heated composition onto a metal sheet and allowing it to cool. The cooled film is then "crumbled" or "scraped" into small flakes by any type of mechanical process. Thus, a successful composition must possess two properties. First, the composition must possess the property of being easily poured onto the sheet, thus forming a thin film. Second, once the composition is allowed to cool, it must break into flakes after crumpling or scraping. These flakes are consequently easily stored and re-melted as necessary.

Pastillation is a process in which small amounts of the desired formulation are dispensed into pastilles. These pastilles are then allowed to cool, forming a product, which is in solid form, but easily returned to liquid state. Whether a formulation is capable of pastillation is measurable by distributing small amounts of the heated formulation into pastilles. These pastilles are then allowed to cool. The pastilles must be easily melted without tremendous amounts of heat, preferably below the boiling point of water.

In one aspect of the present invention, the ante-iso fatty acid content in quat mixtures is enriched by adding relatively pure ante-iso fatty acids to an existing mixture. Where enrichment of the ante-iso fatty acid content is accomplished by adding ante-iso fatty acids to an existing mixture of fatty acid species, such as lanolin, the resulting mixture will contain hydroxy fatty acids; however, their relative percentage will be accordingly reduced. In this context, "enriched" generally should be construed as containing an amount greater than the amount of ante-iso fatty acids contained in lanolin, and more preferably about 10% greater than the amount of ante-iso fatty acids contained in comparable lanolin mixtures and compositions. An additive for personal care products including hair care products (shampoos and conditioners) skin care products and cosmetics containing quats produced from these ante-iso enriched fatty acid mixtures is also an aspect of the invention.

In another aspect of the present invention there is provided an additive for hair care, cosmetic and skin care products which consists essentially of quaternary compounds of ante-iso fatty acids. In this context, the term "consisting essentially of" should be construed as excluding other fatty acid species commonly found in lanolin such as hydroxy fatty acids, unsubstituted or normal fatty acids and iso fatty acids. These should be present, if at all, in as small an amount as possible and, preferably, in less than a total of 15% by weight of the additive.

Another aspect of the present invention is an additive for such personal care products consisting essentially of 18-MEA. "Consisting essentially of" in this context allows for the presence of up to 20% of other ante-iso fatty acid quats and up to 15% of quats based on hydroxy fatty acids, unsubstituted fatty acids and/or iso fatty acids. Personal care products containing any of the above additives are also specifically contemplated.

Finally, the quats and in particular, the additives produced from the quats in accordance with the present invention are preferably compatible with anionic surfactants. It is to be understood that not all of these quats are compatible with anionic surfactants. For example, certain dialkyl quats disclosed in the '204 application are not compatible. Generally those dialkyl quats without free hydroxy groups attached to the fatty acids used to quarternize the N atom of the amide will not be compatible with anionic surfactants. Additionally, benzyl quats in accordance with the '203 application are also generally not compatible with anionic surfactants.

In addition to the quats and solvents, additives for personal care products in accordance with the present invention can include other quat formulations such as those described in the '203 and '204 application (resulting in hybrid blends), fatty alcohols with $C_{12}$-$C_{22}$ chains (promoting flakeability), glycols (for handling), as well as protein additives. The resulting quat formulations and resulting blends can potentially be used in a variety of skin and hair care products including, but not limited to, ointments, lotions, anti-bacterial products, shampoos, conditioners, shaving preparations, etc.

The quat additives of the present invention are added to these personal care products, generally in an amount sufficient to provide a cationic activity (on an active basis) of between about 0.5% to about 10% by weight. These quat additives are useful in products such as shampoos, conditioners, skin care products and the like. Preferably, the additives comprise no more than 10% quaternized hydroxy fatty acids.

EXAMPLES

Examples I-III show the typical process for producing a quat formulation according to the present invention. Example IV combines the quat formulation according to the present invention with behenyl trimethyl ammonium methosulfate and cetearyl alcohol to produce an exemplary hybrid blend product. Table IV shows the fatty acid composition used to prepare the final solutions of Examples III and IV.

TABLE IV

| Carbon Chain | Ante-iso Acids(%) | Normal Acids(%) | Iso-Acids |
|---|---|---|---|
| $C_{14}$ | 0 | 0.15 | 0.16 |
| $C_{15}$ | 0.59 | Traces | Traces |
| $C_{16}$ | 0.19 | 1.45 | 1.34 |
| $C_{17}$ | Traces | Traces | 2.48 |
| $C_{18}$ | 1.99 | 3.69 | 4.66 |
| $C_{19}$ | 9.10 | 0.19 | 0.59 |
| $C_{20}$ | 0 | 2.11 | 11.79 |
| $C_{21}$ | 12.34 | 0 | 0.55 |

TABLE IV-continued

| Carbon Chain | Ante-iso Acids(%) | Normal Acids(%) | Iso-Acids |
|---|---|---|---|
| $C_{22}$ | 0 | 2.40 | 5.17 |
| $C_{23}$ | 4.87 | 0 | 0.47 |
| $C_{24}$ | 0 | 6.2 | 4.93 |
| $C_{25}$ | 6.24 | 0.36 | 0.60 |
| $C_{26}$ | 0 | 1.57 | 2.95 |
| $C_{27}$ | 0.97 | 0 | 0 |
| TOTAL(% w/w) | 36.3 | 18.1 | 35.7 |

Example I

Preparation of alkyl amidoamine 1058.42 grams (3.324 moles) of the acid mixture conforming to Table IV above was charged to a glass reaction vessel equipped with a stirrer, thermometer, condenser and nitrogen sparge. With the temperature at 60-68° C., 441.58 grams (4.329 moles) of dimethylaminopropylamine were added and the reaction mass heated to 150-180° C. The batch was reacted at 150-180° C. until the acid value was 7.2 mg KOH. Vacuum was then applied to remove excess dimethylaminopropylamine. The final product had an acid value of 3.9 mg KOH, a base value of 134 mg KOH and a melt point of 42-45° C.

Example II

Quaternization of alkyl amidoamine from Example I 329.35 grams (0.8236 moles) of alkyl-amidoamine from Example I were charged to a glass reaction vessel equipped with a stirrer, thermometer, condenser and nitrogen sparge. The product was heated to 60° C. and 50 grams of butylene glycol added. 126.42 grams (0.82 moles) of diethyl sulfate were slowly added while stirring. The batch was kept at 75-80° C. for 3 hours. The final acid value was 8.7 mg KOH and the base value was 2.8 mg KOH. The final formulation was a soft solid with 90% cationic activity.

Example III

Preparations of liquid quats 150 grams of the formulation from Example II was diluted with water to obtain a product with 30% cationic activity. This additive was liquid at room temperature and was found to be compatible with anionic surfactants.

The ante-iso quat formulation produced in Example II was also blended with behenyl trimethyl ammonium methosulfate and cetearyl alcohol to produce a 45% cationic actives, flakeable product. This composition did not lend itself to be incorporated into a clear shampoo, but is useful in hair conditioners where it provides for easy emulsification and self bodying effects to the formulation, while providing the desired properties of the ante-iso quat.

Example IV

Comparative Example

The quat formulation of Example III having a 30% cationic activity was then tested against a quat mixture made from lanolin quats (produced by the methods described in Examples I and II) as described in Table III. Tresses prepared from virgin brown hair obtained from International Hair Importers & Products Inc. (70 Westmoreland Ave., White Plains, N.Y.) were treated with 1.5% actives solutions (produced with water) of the compositions described in Example III and Table III. Three tresses were used for each evaluation. The tresses were tested for wet combing force reduction and compared to dry, untreated tresses using a Dia-Stron Miniature Tensile Tester. Table VI shows the average results obtained from three separate measurements of the reduction in combing force for Example III and Table III (Lanolin quat) compositions:

TABLE V

|  | Virgin tresses/ Example III Composition | Virgin tresses/ Lanolin quat Composition |
|---|---|---|
| % Average reduction in peak combing force (gmf) | 97.5 | 75.4 |

The percentage reduction of wet combing force is intended to compare to the force required to comb a tress of hair that is competely dry with a tress of hair that is wet and consequently much tougher to comb through. A 100% reduction in wet combing force means that the force required is the same as that of dry hair. This is the ideal result.

Table V shows that the quat mixtures according to the present invention reduced the wet combing force on virgin hair tresses by 97.5% compared to a 75.4% reduction by the lanolin acid analogue of Table III. As noted in table III, the lanolin analogue began with a total of approximately 35% hydroxy and iso-hydroxy acids and 17.67% ante-iso acids, while the preferred ante-iso quat mixture created from the composition shown in Table IV possessed approximately 36% ante-iso acids and substantially no hydroxy or iso-hydroxy acids. Thus, the elimination of the hydroxy or iso-hydroxy acids along with an increase in ante-iso acid concentration of approximately 18% resulted in a 22% decrease in the peak combing force.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invnetion as defined by the appended claims.

We claim:

1. A personal care product comprising: at least one carrier and quaternary ammonium compounds comprising quaternary ante-iso fatty acids in an amount about 8% to about 95% by weight based on the total weight of said quaternary ammonium compounds, quaternary normal fatty acids in an amount about 1.5% to about 50% by weight based on the total weight of said quaternary ammonium compounds, and quaternary iso fatty acids in an amount about 3.5% to about 60% by weight based on the total weight of said quaternary ammonium compounds, wherein said quaternary ammonium compounds are present in an amount sufficient to provide a cationic activity in said personal care product, on an active basis, of about 0.5% to about 10% by weight of said personal care product; and wherein said quaternary ammonium compounds include no more than 10% quaternized hydroxy fatty acids.

2. The personal care product of claim 1, wherein said carrier is a liquid capable of solubilizing said quaternary ammonium compounds.

3. The personal care product of claim 1, wherein said carrier is compatible with anionic surfactants.

4. The personal care product of claim 1 which is a shampoo, conditioner or skin product.

5. The personal care product of claim 1, wherein said quaternary ante-iso fatty acids are provided in an amount about 15% to about 75% by weight based on the total weight of said quaternary ammonium compounds, said quaternary normal fatty acids are provided in an amount about 10% to about 50% by weight based on the total weight of said quaternary ammonium compounds, and said quaternary iso fatty acids are provided in an amount about 10% to about 50% by weight based on the total weight of said quaternary ammonium compounds.

6. A personal care product according to claim 1 comprising quaternary compounds of the formula (II):

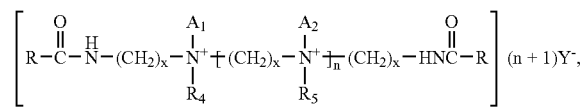

wherein at least one of R is

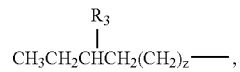

$R_3$ is an alkyl group, straight chain or branched, saturated or unsaturated, z may vary from 0 to 30; each $A_1$ and $A_2$, same or different, are independently alkoxy or lower alkyl; z may vary from 0 to 30; $R_4$ and $R_5$ are alkyl groups, same or different; n may range from 0 to 10, x may range from 1 to 6; $Y^-$ are counter ions; if only one R is

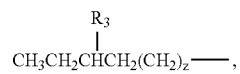

then the other R is an alkyl group, straight chain or branched, aromatic or aliphatic, saturated or unsaturated, substituted or un-substituted, having up to 30 carbon atoms.

7. The personal care product of claim 6, wherein at least one R is derived from 18-methyl eicosanoic acid (18-MEA).

8. The personal care product of claim 6, wherein both R groups are derived from 18-methyl eicosanoic acid (18-MEA).

9. The personal care product of claim 6 which is a shampoo, conditioner or skin product.

10. The personal care product of claim 6, wherein when R is

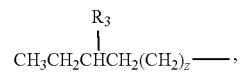

it has from 8 to 30 carbon atoms; $R_4$ and $R_5$ are lower alkyl groups; $A_1$ and $A_2$, same or different, are each independently ethoxy, polyethoxy, propoxy, methyl or lower alkyl having from 1 to 6 carbon atoms; $R_3$ is a lower alkyl group having up to 12 carbon atoms; $Y^-$ are nitrogen-, sulfur- or halogen-containing anions; if only one R is

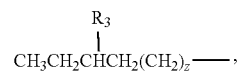

then the other R is an aliphatic alkyl group having 12 to 24 carbon atoms.

11. The personal care product of claim 10, wherein when R is

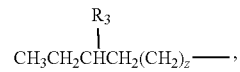

it has from 8 to 30 carbon atoms; $R_3$ is a lower alkyl group having from 1 to 6 carbon atoms; $R_4$ and $R_5$ are independently methyl or ethyl; $Y^-$ are halogens, sulfates, sulfites, sulfides, or nitro anions; if only one R is

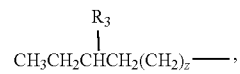

then the other R is an aliphatic alkyl group having 14 to 22 carbon atoms.

12. The personal care product of claim 11, wherein $R_3$, $R_4$ and $R_5$ are methyl.

13. A personal care product according to claim 1 comprising a carrier and one or more quaternized ante-iso acid compounds consisting essentially of quaternary compounds of the formula (II):

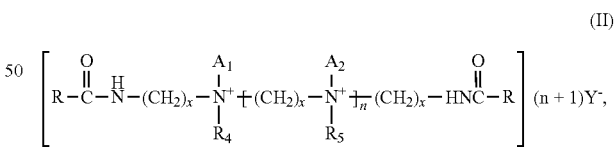

wherein at least one of R is

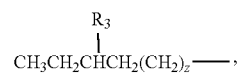

$R_3$ is an alkyl group, straight chain or branched, saturated or unsaturated, having up to 12 carbon atoms, z may vary from 0 to 30; each $A_1$ and $A_2$, same or different, are independently alkoxy or lower alkyl group having 1 to 6 carbon atoms; z may vary from 0 to 30; $R_4$ and $R_5$ are alkyl groups, same or different, having up to 6 carbon atoms; n may range from 0 to 10, x may range from 1 to 6; Y⁻ are counter ions selected from the group consisting of nitrogen-containing, sulfur-containing and halogen-containing anions; if only one R is

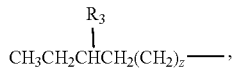

then another R is an alkyl group, straight chain or branched, aromatic or aliphatic, saturated or unsaturated, substituted or un-substituted, having up to 30 carbon atoms.

14. The personal care product of claim 13 which is a shampoo, conditioner or skin product.

15. A personal care product according to claim 1 comprising a carrier and quaternary ammonium compounds further comprising one or more quaternized ante-iso compounds of the formula (III):

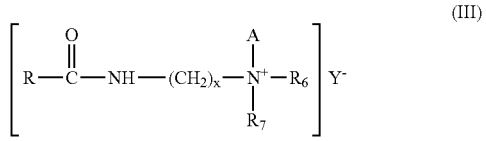

in an amount about 8% to about 95% by weight based on the total weight of said quaternary ammonium compounds, quaternary normal fatty acids in an amount about 1.5% to about 50% by weight based on the total weight of said quaternary ammonium compounds, and quaternary iso fatty acids in an amount about 3.5% to about 60% by weight based on the total weight of said quaternary ammonium compounds;
wherein R is

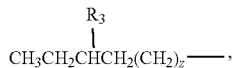

$R_3$ is an alkyl group, straight chain or branched, saturated or unsaturated, having up to 12 carbon atoms, z may vary from 0 to 30; $R_6$ and $R_7$, same or different, are each independently aromatic or aliphatic alkyl group, straight chain or branched, saturated or unsaturated, having 1 to 8 carbon atoms, or an alkoxy group; x ranges from 1 to 6; A is alkoxy or lower alkyl having 1 to 6 carbon atoms; Y⁻ is a counter ion selected from the group consisting of nitrogen-containing, sulfur-containing and halogen-containing anions;

wherein said quaternary ammonium compounds are present in an amount sufficient to provide a cationic activity in said personal care product, on an active basis, of about 0.5% to about 10% by weight of said personal care product; and wherein said quaternary ammonium compounds include no more than about 10% quaternized hydroxy fatty acids.

16. The personal care product of claim 15, wherein said quaternized ante-iso compounds are provided in an amount about 15% to about 75% by weight based on the total weight of said quaternary ammonium compounds, said quaternary normal fatty acids are provided in an amount about 10% to about 50% by weight based on the total weight of said quaternary ammonium compounds, and said quaternary iso fatty acids are provided in an amount about 10% to about 50% by weight based on the total weight of said quaternary ammonium compounds.

17. The personal care product of claim 15 which is a shampoo, conditioner or skin product.

18. A personal care product comprising: at least one carrier and quaternary ammonium compounds comprising quaternary ante-iso fatty acids in an amount about 36% by weight based on the total weight of said quaternary ammonium compounds, quaternary normal fatty acids in an amount about 18% by weight based on the total weight of said quaternary ammonium compounds, and quaternary iso fatty acids in an amount about 36% by weight based on the total weight of said quaternary ammonium compounds, wherein said quaternary ammonium compounds are present in an amount sufficient to provide a cationic activity in said personal care product, on an active basis, of about 0.5% to about 10% by weight of said personal care product; and wherein said quaternary ammonium compounds include no more than 10% quaternized hydroxy fatty acids.

* * * * *